United States Patent [19]

McKay

[11] Patent Number: 5,702,449
[45] Date of Patent: Dec. 30, 1997

[54] REINFORCED POROUS SPINAL IMPLANTS

[75] Inventor: William F. McKay, Memphis, Tenn.

[73] Assignee: Danek Medical, Inc., Memphis, Tenn.

[21] Appl. No.: 485,842

[22] Filed: Jun. 7, 1995

[51] Int. Cl.$^6$ .................................................... A61F 2/44
[52] U.S. Cl. ............................................................ 623/17
[58] Field of Search ........................................ 623/16, 17

[56] References Cited

U.S. PATENT DOCUMENTS

| | | | |
|---|---|---|---|
| 4,309,488 | 1/1982 | Heide et al. | 428/547 |
| 4,596,574 | 6/1986 | Urist | 623/16 |
| 4,599,086 | 7/1986 | Doty | 623/17 |
| 4,626,392 | 12/1986 | Kondo et al. | 264/62 |
| 4,636,217 | 1/1987 | Ogilvie et al. | 623/17 |
| 4,654,314 | 3/1987 | Takagi et al. | 501/82 |
| 4,687,675 | 8/1987 | Nakano et al. | 427/2 |
| 4,714,469 | 12/1987 | Kenna | 623/17 |
| 4,722,870 | 2/1988 | White | 428/621 |
| 4,820,305 | 4/1989 | Harms et al. | 623/16 |
| 4,834,757 | 5/1989 | Brantigan | 623/17 |
| 4,878,915 | 11/1989 | Brantigan | 623/17 |
| 4,917,703 | 4/1990 | Albrektsson | 623/66 |
| 4,961,740 | 10/1990 | Ray et al. | 606/61 |
| 4,976,738 | 12/1990 | Frey et al. | 623/16 |
| 5,002,583 | 3/1991 | Pitaru et al. | 623/66 |
| 5,015,247 | 5/1991 | Michelson | 606/61 |
| 5,026,373 | 6/1991 | Ray et al. | 606/61 |
| 5,055,104 | 10/1991 | Ray | 606/61 |
| 5,147,402 | 9/1992 | Bohler et al. | 623/16 |
| 5,152,791 | 10/1992 | Hakamatsuka et al. | 623/16 |
| 5,219,363 | 6/1993 | Croninshield et al. | 623/23 |
| 5,258,029 | 11/1993 | Chu et al. | 623/16 |
| 5,282,861 | 2/1994 | Kaplan | 623/16 |
| 5,306,302 | 4/1994 | Bauer et al. | 623/16 |
| 5,306,303 | 4/1994 | Lynch | 623/16 |
| 5,306,307 | 4/1994 | Senter et al. | 623/17 |
| 5,330,826 | 7/1994 | Taylor et al. | 428/216 |
| 5,346,492 | 9/1994 | Morgan | 606/60 |

FOREIGN PATENT DOCUMENTS 0179695  4/1986  European Pat. Off. .

OTHER PUBLICATIONS

*Evaluation of Porous Biphasic Calcium Phosphate Ceramics for Anterior Cervical Interbody Fusion in a Caprine Model*, Toth, An, Lim, Ran, Weiss, Lundberg, Xu, Lynch; Spine, vol. 20, No. 20, pp. 2203–2210, 1995.

*Anterior Cervical Discectomy and Vertebral Interbody Fusion with Hydroxy-Apatite Ceramic. Preliminary Results.*, D. K. Boker, R. Schultheib, D. van Roose, B. Kaden; Acta Neurochirurgica, Spring 1993.

*Osteogenesis by Subcutaneous Implantation of Calcium Phosphates—A Histological Description*, J. M. Toth, K. L. Lynch, and D. A. Hackbarth, 39th Annual Meeting, Orthopaedic Research Society, Feb. 15–18, 1993.

*The Influence of Multiphase Calcium Phosphate Bioceramics on Bone Formation in Nonosseous Tissues*, Li. Yubao, Zhang Xingdong, Chen Weiqun, Liu Yuhua, 19th Annual Meeting of the Society for Biomaterials, Apr. 28–May 2, 1993.

*Osteoinductivity by Subcutaneous Implantation of a Fibrillar Collagen and a Calcium Phosphate Ceramic Composite*, K. L. Lynch, J. M. Toth, K. R. Hamson, K. C. Ho, W. M. Hirthe, Presented Nov., 1990.

(List continued on next page.)

*Primary Examiner*—Randy C. Shay
*Attorney, Agent, or Firm*—Woodard, Emhardt, Naughton, Moriarty & McNett

[57] ABSTRACT

One embodiment of a spinal implant 10 includes a body 11 sized and configured for engagement between adjacent vertebrae V. The body 11 includes two opposite faces 12, 14 and an outer surface 13 between the two faces 12, 14. The body 11 includes a porous biocompatible material for permitting tissue ingrowth therethrough. A sleeve 15 is disposed around the outer surface 13 of the body 11. The sleeve 15 is composed of a second material which is relatively stronger under compressive loads than the biocompatible material of the body 11. Also provided is a plurality of apertures 16 through the sleeve 15 in communication with the outer surface 13 of the body 11 for bone ingrowth. Means for attaching the sleeve to the endplates of adjoining vertebral bodies are also provided.

26 Claims, 6 Drawing Sheets

OTHER PUBLICATIONS

*Ceramic Anterior Spinal Fusion: Biological and Biomechanical Comparison in a Canine Model*, S. e. Emery, D. A. Fuller, J. S. Bensusan, S. Stevenson, 40th Annual Meeting, Orthopaedic Research Society, Feb. 21–24, 1994.

*Osteoinductivity by Calcium Phosphate Ceramics*, J. M. Toth, K. L. Lynch and K. R. Hamson, Fourth World Biomaterials Congress, Apr. 24–28, 1992.

*Evaluation of Collagen/Ceramic Bone Graft Substitutes With Osteoinductive Composites in Dogs with Segmental Spinal Instrumentation*, T. J. Flatley, K. L. Lynch, D. A. Ladwig, D. A. Skrade, Papers #74, 25th Annual Meeting, Scoliosis Research Society Sep. 23–27, 1990.

*Macroporous Biphasic Calcium Phosphate as a Bone Substitute for Postero–Lateral Spine Fusion. Biomechanical Evaluation in Sheep*. P. Guigui, P. Y. Plais, D. Chopin, F. Lavaste, P. Hardouin, ISSLS Jun. 15–19, 1993.

*Bioceramics*, P. Ducheyne, D. Christiansen, vol. 6, pp. 9–14, Nov., 1993.

*Stiffness Evaluation*, J. Delecrin, N. Passuti, J. Royer, G. Daculsi and Y. Maugars, Fourth World Biomaterials Congress, Apr. 24–28, 1992.

*Comparison of Compressive Strengths of Iliac Bone Grafts and Porous Calcium Phosphate Ceramics for Spinal Fusion*, J. M. Toth, T. H. Lim, H. S. An, R. Xu, Y. Ran, and L. M. McGrady, 40th Annual Meeting, Orthopaedic Research Society, Feb. 21–24, 1994.

*Ceramic–Induced Osteogenesis Following Subcutaneous Implantation of Calcium Phosphates*, J. M. Toth, K.L. Lynch and D. A. Hackbarth, Bioceramics, vol. 6, pp. 9–14, Nov., 1993.

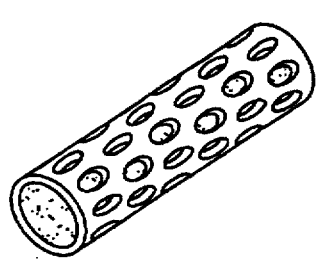
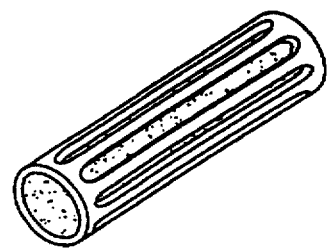
Fig. 6   Fig. 7
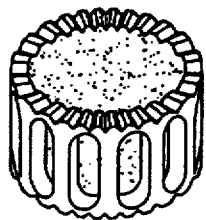
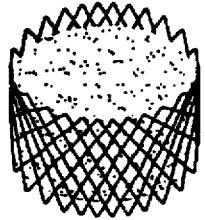
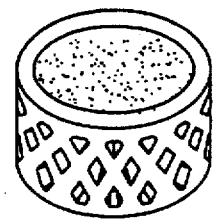
Fig. 8   Fig. 9   Fig. 10
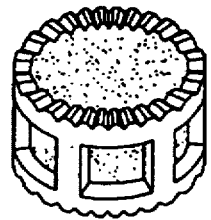
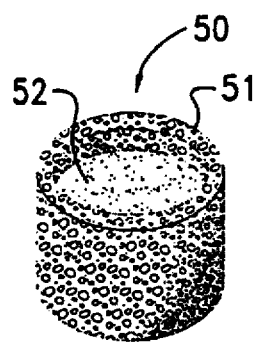
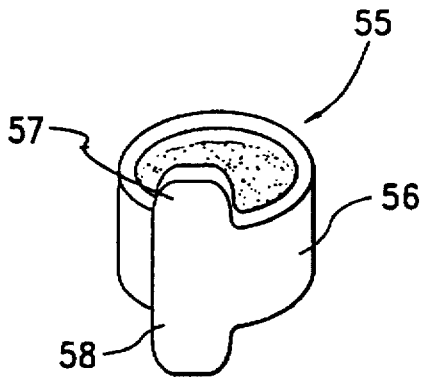
Fig. 11   Fig. 12   Fig. 13

REINFORCED POROUS SPINAL IMPLANTS

FIELD OF THE INVENTION

The present invention broadly concerns devices for stabilizing the spine and devices for implantation between vertebrae, and more particularly in the intradiscal space. Specifically, the invention concerns a reinforced, porous spinal implant.

BACKGROUND OF THE INVENTION

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusions of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Prosthetic implants are often used to prevent collapse of the space. The implant must provide temporary support and allow bone ingrowth. Success of the discectomy and fusion procedure requires the development of a contiguous growth of bone to create a solid mass because the implant may not withstand the compressive loads on the spine for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; U.S. Pat. No. 5,015,247 to Michelson and U.S. Pat. No. 4,820,305 to Harms et al. teach hollow metal cage structures. There are several disadvantages associated with the use of these metal implants. Solid body metal implants do not allow bone ingrowth which may lead to the eventual failure of the implant. Surface porosity in such solid implants does not correct this problem because it will not allow sufficient ingrowth to provide a solid bone mass strong enough to withstand the loads of the spine. On the other hand, the hollow cage structures of Harms, Ray and Michelson allow ingrowth. These devices can also be filled with bone graft material to promote bone growth. Unfortunately, many of these devices are difficult to machine and therefore expensive. Furthermore, metal implants may stress shield the bone graft, increasing the time required for fusion to occur.

The Michelson implant further requires a special tool and additional preparation of the adjacent vertebral bodies to ensure fusion. A special press is required to forcibly inject a compressed core of osteogenic material into the device. The osteogenic material, which is removed from the patient's iliac crest, must be compressed so that the graft material extends through openings in the implant whereby the graft material directly contacts the bone of the adjacent vertebral bodies. Michelson also requires coring out an area of each adjacent vertebral body to provide sufficient surface area of contact between the implant and the cortical bone of the vertebrae.

The use of bone graft materials in these past metal cage fusion devices presents several disadvantages. Autografts, bone material surgically removed from the patient, are undesirable because they may not yield a sufficient quantity of graft material. The additional surgery to extract the autograft also increases the risk of infection and may reduce structural integrity at the donor site. The supply of allograft material, which is obtained from donors of the same species, is not limited. However, allografts are also disadvantageous because of the risk of disease transmission and immune reactions. Furthermore, allogenic bone does not have the osteogenic potential of autogenous bone and therefore will give only temporary support.

Due to the need for safer bone graft materials, bone graft substitutes, such as bioceramics have recently received considerable attention. Calcium phosphate ceramics are biocompatible and do not present the infectious or immunological concerns of allograft materials. Ceramics may be prepared in any quantity which is a great advantage over autograft bone graft material. Furthermore, bioceramics are osteoconductive, stimulating osteogenesis in boney sites, and are also thought to be osteogenic, able to initiate osteogenesis in non-boney sites. Bioceramics provide a porous matrix which further encourages new bone growth. Unfortunately, ceramic implants lack the strength to support high spinal loads and therefore require separate fixation before the fusion.

Of the calcium phosphate ceramics, hydroxyapatite and tricalcium phosphate ceramics have been most commonly used for bone grafting. Hydroxyapatite is chemically similar to inorganic bone substance and biocompatible with bone. However, it is slowly degraded. β-tricalcium phosphate is rapidly degraded in vivo and is too weak to provide any support. These ceramics have proven unsatisfactory for providing temporary support after discectomy while awaiting fusion.

A need has remained for fusion devices which encourage bone ingrowth and avoid stress shielding yet provide sufficient strength to support the vertebral column until the adjacent vertebrae are fused.

SUMMARY OF THE INVENTION

In accordance with the invention, a spinal implant is provided for engagement between vertebrae. The implant includes a body sized and configured to fill the space between the vertebrae and having two opposite faces and an outer surface between the two faces. The body includes a porous biocompatible material for permitting tissue ingrowth therethrough. A sleeve is disposed around the outer surface of the body. The sleeve is composed of a second material which is relatively more rigid than the biocompatible material of the body. The invention also contemplates an interbody fusion device having a height approximating the height of a human disc space. In another specific embodiment, a vertebral body replacement device is provided for restoring the space left by the removal of a defective spinal element located between adjoining healthy vertebral bodies.

In one specific embodiment of the invention, there is provided a plurality of apertures through the sleeve in communication with the outer surface of the body for bone ingrowth. In another embodiment, the sleeve is formed of a temperature responsive material such that the chamber has a first inner dimension that is slightly larger than an outer dimension of the body when the sleeve is in a heated state to slidably receive the body within the sleeve. The chamber has a second inner dimension that is slightly smaller than the body when the sleeve is in a cooled state to thereby clamp the body therein.

In another specific embodiment of the invention, there is provided attaching means for attaching the sleeve to the endplates of adjoining vertebral bodies.

One object of the invention is to provide an implant for engagement between vertebrae which encourages bone ingrowth and avoids stress shielding. Another object of the invention is to provide an implant which restores the intervertebral disc space and supports the vertebral column while promoting bone ingrowth. A further object is to provide a vertebral body replacement device for use in restoring the space left by the removal of a defective spinal element while promoting fusion between the adjoining healthy vertebral bodies.

One benefit of the implants of the present invention is that they combine the advantages of ceramics and other porous, biocompatible materials with the advantages of metals, without the corresponding disadvantages. An additional benefit is that the invention provides a stable scaffold for bone ingrowth before fusion occurs. Other objects and further benefits of the present invention will become apparent to persons of ordinary skill in the art from the following written description and accompanying Figures.

BRIEF DESCRIPTION OF THE DRAWINGS

FIGS. 5-13 are alternate embodiments of the implant of FIG. 1.

DESCRIPTION OF THE PREFERRED EMBODIMENTS

Figure 1:
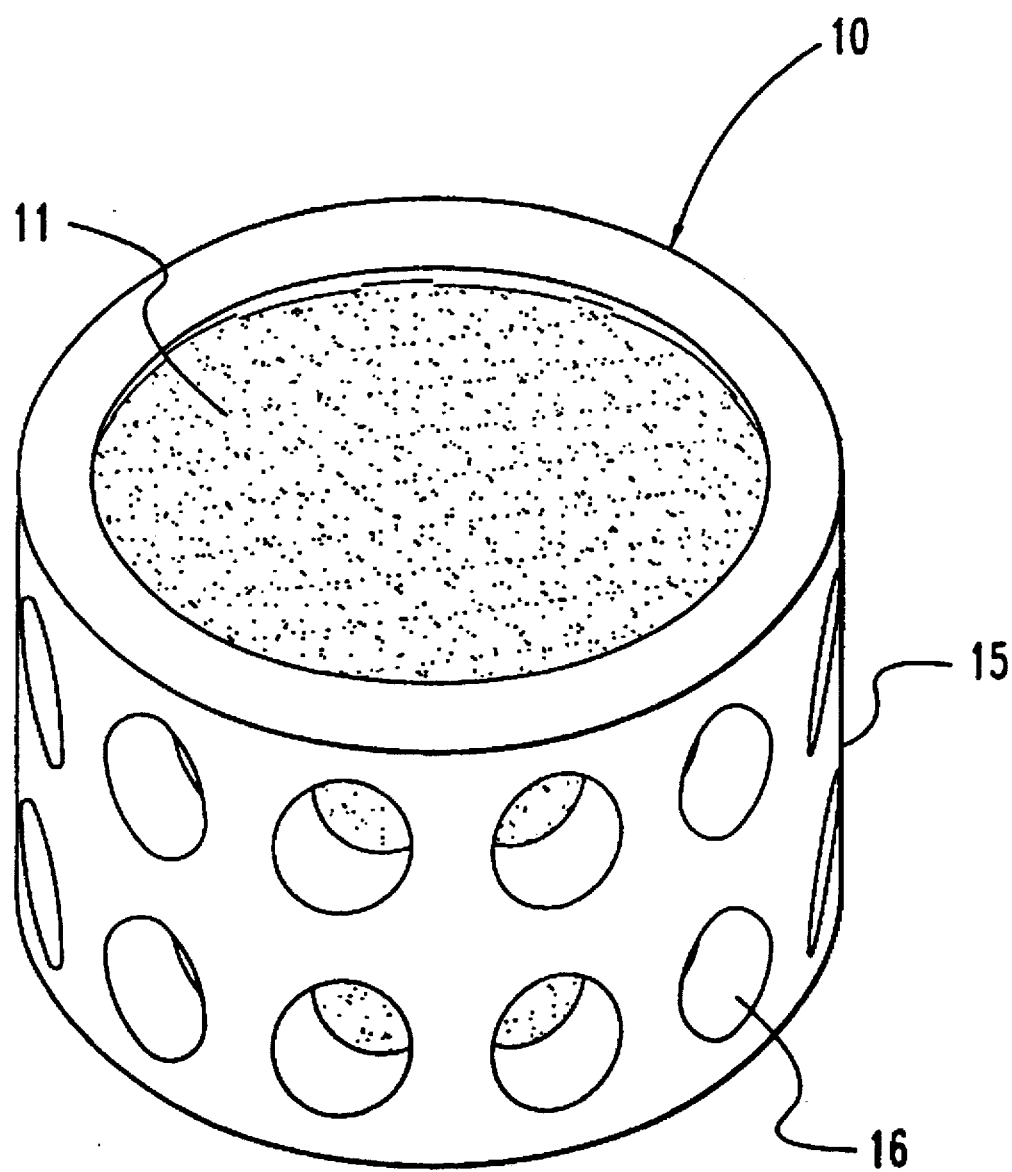
FIG. 1 is a side elevational view of a spinal implant according to one embodiment of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relaters.

The present invention provides spinal implants which include a body composed of a porous biocompatible material reinforced by an outer sleeve made of a second material which is relatively stronger under the compressive load of the spine than the biocompatible material. The inventive implants restore the intervertebral disc space, provide a large surface area for bone ingrowth and eliminate the need for autografts. Implants according to this invention provide immediate load bearing capability and support for the vertebral column without stress shielding the bone implant material.

Figure 2:
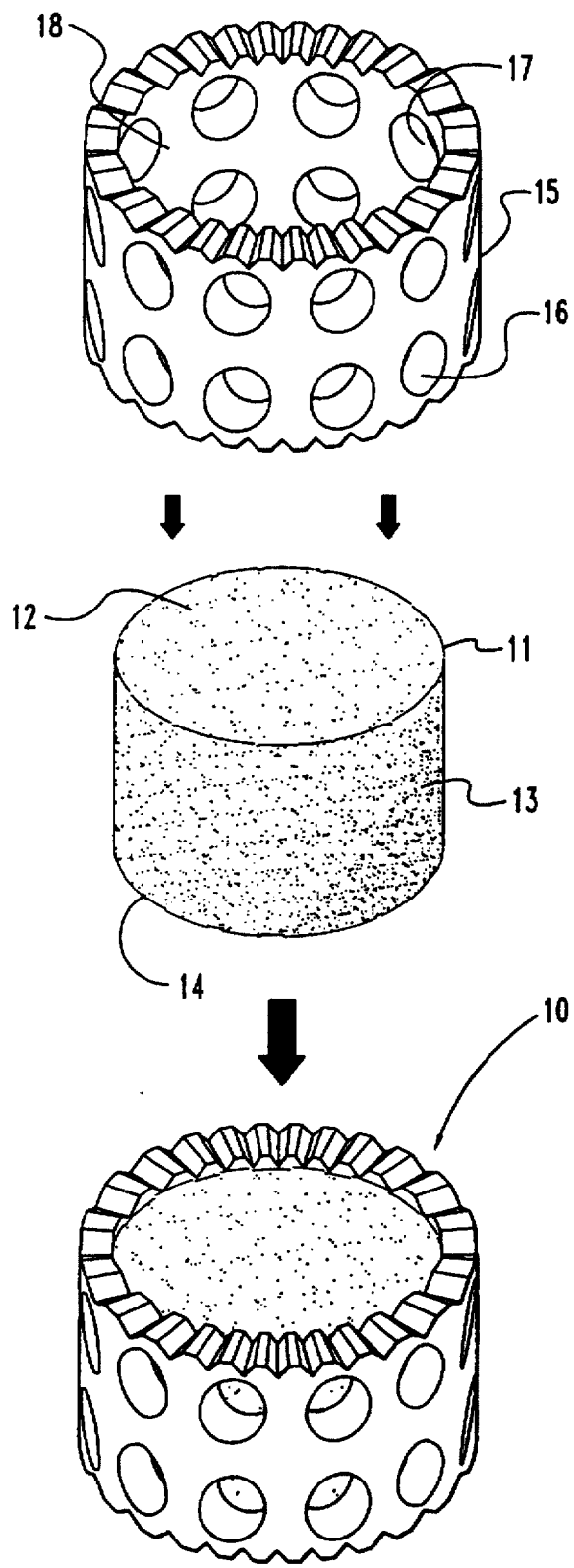
FIG. 2 is an exploded view of the implant of FIG. 1

A spinal implant 10 for engagement between vertebrae in accordance with a preferred embodiment of the present invention is depicted in FIGS. 1 and 2. The implant 10 includes a body 11 composed of a porous biocompatible material for permitting tissue ingrowth therethrough. The body 11 includes two opposite faces 12, 14 and an outer surface 13 disposed between the two faces 12, 14. The body 11 is sized and configured for engagement between two vertebrae V, as shown in FIGS. 3 and 4.

Figure 3:
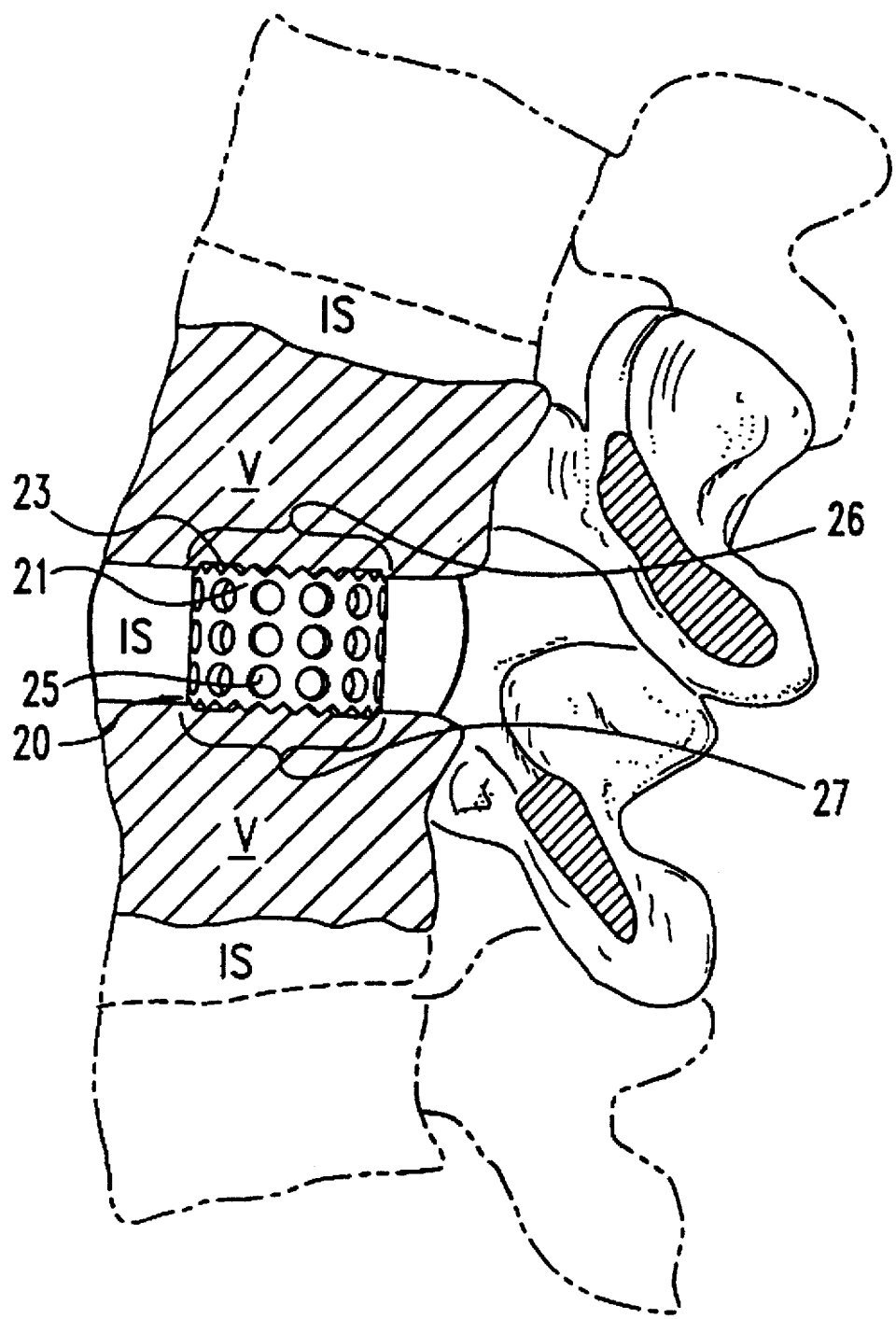
FIG. 3 is a partial side sectional view of a spinal column having an implanted cylindrical interbody fusion device.
Figure 5:
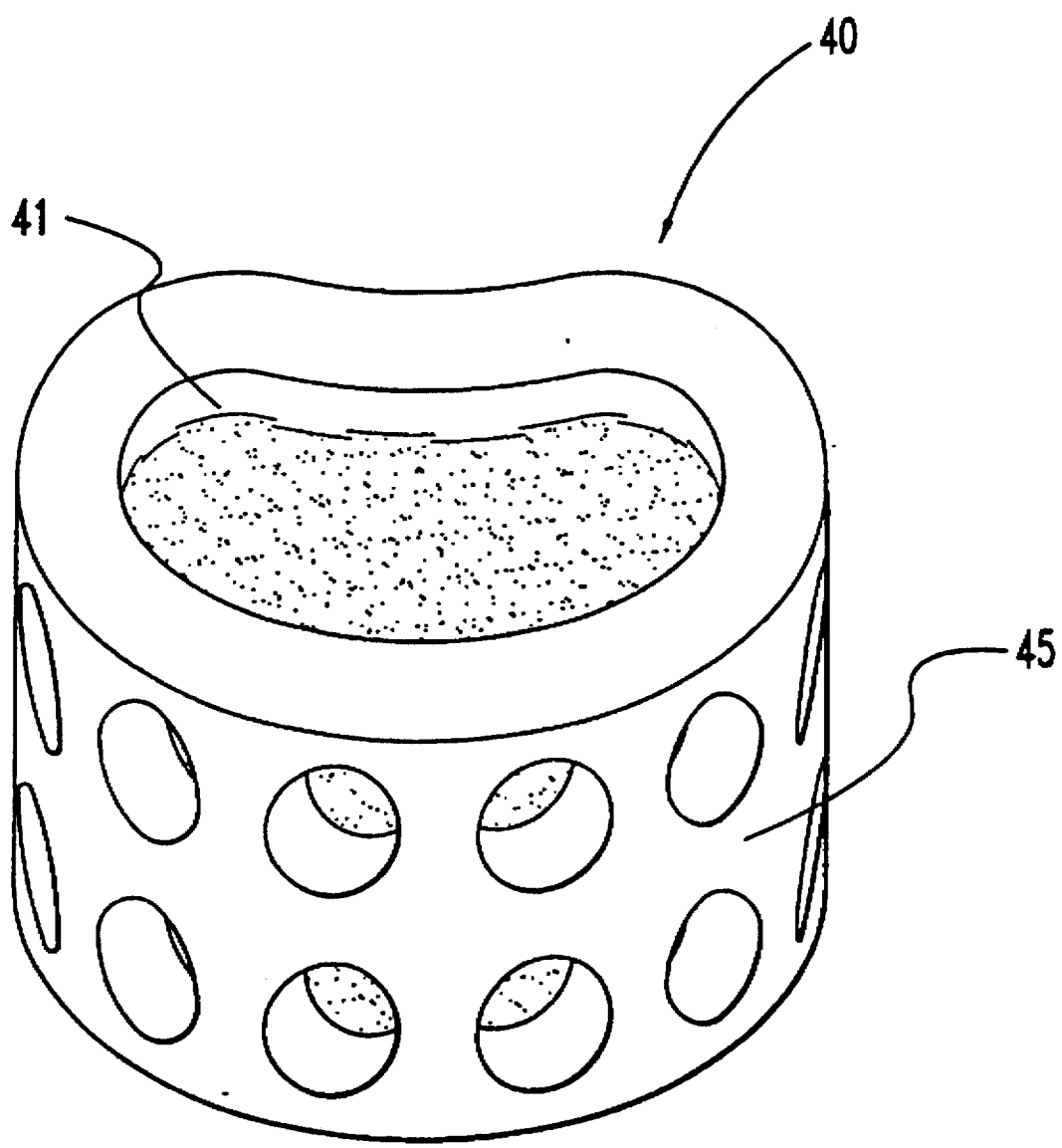

FIG. 3 shows an interbody fusion device 20 according to this invention engaged within the intervertebral space IS between two vertebrae V. Preferably, the body 25 has a height approximating the height of a human disc space IS, and the opposite faces 26, 27 of the body each have a size and shape corresponding to the endplates of each of the vertebrae V. As shown in FIG. 5, the body 41 may have a kidney-shaped cross-section which approximates the size and shape of a nucleus pulposus which has been removed from an intervertebral disc, or the complete disc or vertebral endplate. In the embodiment shown in FIG. 3, the body is preferably sized and shaped to fit snugly within the space IS defined by the endplates and annuli of the adjacent vertebral bodies V. An alternate shape for the body is shown in FIGS. 6 and 7. In some applications, it may be preferable that the height of the body 25 be slightly larger than the height of a human disc space IS to preserve disc space height under the compressive forces of the spine and to avoid the effects of boney erosion.

Figure 4:
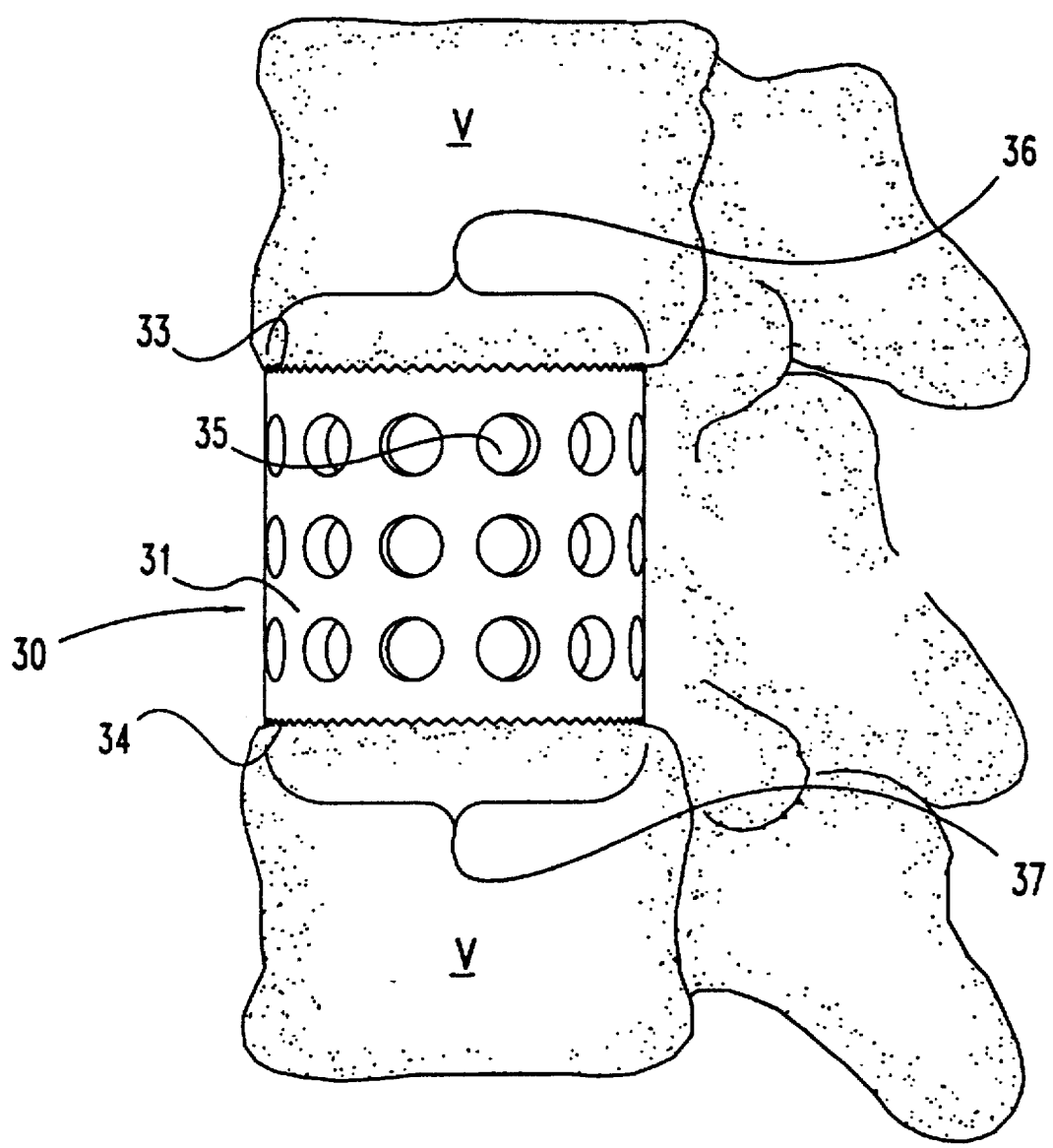
FIG. 4 is a partial side elevational view of a spinal column having an implanted cylindrical vertebral body replacement device.

The invention also contemplates vertebral body replacement devices 30 for use in restoring the space left by the removal of a defective spinal element located between adjoining healthy vertebral bodies V as shown in FIG. 4. In such cases, the body 35 is configured to be locatable within the space between the adjoining vertebral bodies V. The invention contemplates that the body 35 may be any shape or size which is desirable for a spinal implant for engagement between vertebrae V.

The body is composed of a porous biocompatible material for encouraging bone ingrowth. Any porous biocompatible material is contemplated. Such materials and methods of preparing them are well known in the art. Bioceramics are preferred because they exhibit bioactive osteoconductivity. Calcium phosphate ceramics such as hydroxyapatite tricalcium phosphate, tetracalcium phosphate, $\alpha$ calcium pyrophosphate, $\beta$ calcium pyrophosphate and mixtures thereof are preferred. It is contemplated that the biocompatible material may include collagen-ceramic composites as described in Toth, 1993 or ceramic-growth factor composites. Preferably, the ceramic-growth factor composite would be a ceramic-bone morphogenic protein (BMP) composite. BMP can be delivered to the fusion site via pores of the ceramic.

Biphasic calcium phosphate composites are preferred for optimal bone ingrowth and strength and may be prepared according to methods known in the art. (Dilecrin, 1992; Yubaoi 1993; Xingdong, 1993). The biphasic composites may include from about 10% to about 90% hydroxyapatite and about 90% to about 10% by weight of a resorbable calcium phosphate. Hydroxyapatite/$\beta$-tricalcium phosphate (HA/TCP) biphasic osteoconductive ceramics are particularly preferred as described in U.S. Pat. No. 5,306,303 to Lynch. This biphasic ceramic is biomechanically superior to the human tricortical iliac crest under compressive loading. Fusion rates with this ceramic with porosities of 30%, 50% and 70% have been found to be superior to the iliac crest autograft in a goat model. (An et al., 1995).

The ratio of HA/TCP affects the rate of biodegradability. Hydroxyapatite provides strength but it is slowly degraded. β-tricalcium phosphate is relatively weak and rapidly degraded. HA/TCP biphasic ceramics may include from about 10% to about 90% hydroxyapatite and from about 90% to about 10% tricalcium phosphate by weight. The ceramic may include 60% hydroxyapatite and 40% tricalcium phosphate by weight, but most preferably, the ceramic will include 50% hydroxyapatite and 50% tricalcium phosphate by weight.

Porosity of the biocompatible material is required for ingrowth, but it is generally understood that as porosity increases, strength decreases. Implants according to the present invention will optimize porosity with strength requirements to avoid fracture. The biocompatible materials of this invention preferably include porosities of between about 40% and about 60%, with a 50% porosity being most preferred. A pore diameter of at least 200 to 600 microns is required for bone ingrowth. Therefore, the ceramics of the present invention are contemplated to have a mean pore size of about 200 to about 700 microns. Preferably, the mean pore size is about 400 microns.

Referring again to FIGS. 1 and 2, a spinal implant 10 according to this invention includes a sleeve 15 disposed around the outer surface 13 of the body 11. The sleeve 15 is composed of a second material which is relatively stronger under compressive loads than the porous biocompatible material. Preferably, the second material is composed of a metal material. The metal material includes any surgically suitable metal including titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten and alloys thereof. Preferably, the metal is 316 LVM stainless steel, titanium or tantalum foam. Most preferably, the metal material is an open-cell tantalum foam as described in U.S. Pat. No. 5,282,861 to Kaplan. This material is a carbon-metal composite including a skeleton of vitreous carbon defining a network of interconnecting pores which are infiltrated with tantalum or another suitable metal by chemical vapor deposition. This material is advantageous because it provides the strength of other metals to serve as a scaffold and prosthesis but also mimics the structure of bone. The interconnecting pores of the foam serve as another site for bone ingrowth. According to the present invention, a disc of tantalum foam can be prepared according to the Kaplan patent. The center of the tantalum foam disc can then be drilled out to obtain a metal foam sleeve. The implant 50 which is depicted in FIG. 12 can be made from the metal foam sleeve 51 and a suitable body 52.

Referring to FIG. 2, the sleeve 15 includes an inner surface 17 for contacting the outer surface 13 of the body 11. The inner surface 17 of the sleeve 15 defines a chamber 18. Preferably, the sleeve 15 is formed of a temperature responsive material, such as a metal, such that the chamber 18 has a first inner dimension that is slightly larger than an outer dimension of the body 11 when the sleeve 15 is in a heated state. In this state, the sleeve 15 can slidably receive the body 11 therein. The chamber 18 has a second inner dimension that is slightly smaller than the body 11 when the sleeve 15 is in a cooled state to thereby clamp the body 11 therein. In other words, the sleeve 15 can be expanded by the application of heat and then shrunk around the body 11 by cooling. Alternatively, when the body 11 is a ceramic, it can be formed within the chamber 18 of the sleeve 15.

The size and shape of the sleeve 15 corresponds to the configuration of the outer surface 13 of the body 11 as shown in FIGS. 2 and 5–11. For example, when the body is cylindrical, the sleeve is a hollow cylinder as shown in FIGS. 6–11. In one specific embodiment of the invention, the sleeve 15 has a height which is less than a height of the outer surface 13 of the body 11 to permit contact of the opposite faces 12, 14 of the body 11 with endplates of the corresponding vertebrae V when the implant is implanted between the vertebrae V.

Referring to FIG. 1, an implant according to the present invention preferably includes a sleeve 15 which defines a plurality of apertures 16 defined therethrough in communication with the outer surface 13 of the body 11 for bone ingrowth. Any suitable shape is contemplated for the apertures. As shown in FIGS. 6–11, the apertures may be generally circular, oval, diamond shaped or rectangular. However, the size and number of apertures must be controlled to maintain the overall strength of the sleeve 15.

Preferably, the implants of the present invention include attaching means for attaching the sleeve 21, 31 of the implants to the adjoining vertebral bodies V as shown in FIGS. 3 and 4. On one specific embodiment depicted in FIG. 3, the attaching means includes teeth 23 disposed at the superior 26 and inferior 27 ends of the sleeve 21. As shown in FIG. 4, the attaching means may alternatively include roughened surfaces 33, 34 defined on the superior 36 and inferior 37 ends of the sleeve 31. The roughened surfaces can be formed by conventional machining techniques, such as knurling.

In one embodiment, shown in FIG. 13, the sleeve 56 includes stops 57, 58, which contact the adjacent vertebral bodies to prevent the device 55 from slipping forward within the disc space.

In another specific embodiment for use in the cervical spine, the body 11 has a height of 8 mm and a diameter of 11 mm. The sleeve 15 has an overall height of 10 mm, including teeth 23, and a height of slightly over 8 mm between the teeth 23. The sleeve 15 in the specific embodiment has an inner diameter slightly less than 11 mm and a wall thickness of about 1 mm. The sleeve 15 is provided with twenty-four uniformly sized and spaced apertures 16 having a diameter of about 2 mm.

The implants of this invention may be implanted according to surgical procedures which are well known in the art. In addition, the implants can be implanted following a full or partial discectomy of the instrumented disc space.

Implants according to the present invention have compressive strengths sufficient to withstand the normal loads on the spinal column. These inventive implants are at least as strong as tricortical iliac crest grafts. The implants have an ASTM C-773 compressive strength of at least 7 MPa, preferably at least 20 MPa and most preferably at least 40 MPa. Under these loads, the outer sleeve will bear most of the load without bending or fracture, to protect the more brittle and weaker ceramic material within.

Implants according to this invention combine the advantages of porous biocompatible materials with stronger materials such as metals. The implants provide immediate load bearing capability without stress shielding. The sleeve composed of the stronger materials provides a tension band around the porous biocompatible material to prevent fracture of the body. The body carries the initial load and slowly transfers it to the newly formed bone. The porous biocompatible material provides a large surface area for bone ingrowth and eliminates the needs for autograft. Where the biocompatible material is a bioceramic, it will be eventually resorbed and replaced by host bone.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

REFERENCES

The following references are indicative of the level of skill in the art and are hereby incorporated by reference in their entirety as if each had been individually incorporated by reference and fully set forth.

An et al., Porous Biphasic Ceramics for Cervical Fusion, *Spine*, accepted for publication, 1995.

Delecrin et al., Biphasic Calcium Phosphate as a Bone Graft Substitute for Spine Fusion: Stiffness Evaluation, *Fourth World Biomaterials Congress*, 1992 (p. 644).

Li Yubaoi et al., The Influence of Multiphase Calcium Phosphate Bioceramics on Bone Formation in Nonosseous Tissues, *Society for Biomaterials*, 1993 (p. 165).

Toth et al., Ceramic-induced Osteogenesis Following Subcutaneous Implantation of Calcium Phosphates, *Bioceramics*, Vol. 6 ads. Ducheyne & Christianson, 1993 (pp. 9-14).

Toth et al., Comparison of Compressive Strengths of Iliac Bone Grafts and Porous Calcium Phosphate Ceramics for Spine Fusion, *Orthopaedic Research Society*, 1994 (p. 719).

Xingdong et al., Initiation of the Osteoinduction in Calcium Phosphate Ceramics with the Bone Growth Factor, *Society for Biomaterials*, 1993 (p. 299).

U.S. Pat. No. 5,282,861 to Kaplan.

What is claimed:

1. A spinal implant for engagement between vertebrae, comprising:

a body having two opposite faces and an outer surface disposed between said two faces, said body including a porous, biocompatible material for permitting tissue ingrowth therethrough, said body being sized and configured for engagement between two vertebrae; and a sleeve disposed around said outer surface of said body, said sleeve including a second material relatively stronger under compressive loads than said porous, biocompatible material, wherein said sleeve has a height less than a height of said outer surface to permit contact of said opposite faces with endplates of the corresponding vertebrae when the implant is implanted between the vertebrae.

2. The implant of claim 1 wherein said sleeve defines a plurality of apertures therethrough in communication with said outer surface of said body for bone ingrowth.

3. The implant of claim 1 wherein:

said sleeve includes an inner surface for contacting said outer surface of said body, said inner surface of said sleeve defining a chamber;

said sleeve being formed of a temperature responsive material such that said chamber has a first inner dimension that is slightly larger than an outer dimension of said body when said sleeve is in a heated state to slidably receive said body therein; and said chamber has a second inner dimension that is slightly smaller than said body when said sleeve is in a cooled state to thereby clamp said body therein.

4. The implant of claim 1, wherein said sleeve includes:

an inferior end and an opposite superior end; and rigid teeth disposed at each of said inferior and superior ends of said sleeve for engaging the implant to the vertebral bodies.

5. An interbody fusion device, comprising:

a body having an outer surface and a height approximating the height of a human disc space, said body including a porous, biocompatible, biodegradable material for permitting tissue ingrowth therethrough; and a sleeve engaged to said outer surface of said body, said sleeve including a material relatively stronger under compressive loads than said biocompatible material.

6. The implant of claim 5 wherein said implant has an ASTM C-773 compressive strength of at least 7.1 MPa.

7. The implant of claim 6 wherein said implant has a compressive strength of at least 20 MPa.

8. The implant of claim 7 wherein said implant has a compressive strength of at least 40 MPa.

9. The device of claim 5, further comprising:

attaching means for attaching said sleeve to the endplates of the adjacent vertebral bodies.

10. The device of claim 9 wherein:

said sleeve includes an inferior end and a superior end; and said attaching means includes teeth disposed at said superior end and said inferior end of said sleeve.

11. The device of claim 9 wherein:

said sleeve includes an inferior end and a superior end; and said attaching means includes roughened surfaces defined on said superior end and said inferior end of said sleeve.

12. The device of claim 5 wherein said sleeve defines a plurality of apertures therethrough in communication with said outer surface of said body for promoting bone ingrowth.

13. The implant of claim 5 wherein said sleeve is composed of a metal material.

14. The implant of claim 13 wherein said metal material includes a metal selected from the group consisting of tantalum, niobium, hafnium, tungsten and alloys thereof.

15. The implant of claim 14 wherein said metal material is a tantalum foam.

16. The device of claim 13 wherein said metal material includes titanium.

17. The device of claim 5 wherein said body has a kidney-shaped cross-section to conform to the shape of vertebral endplates.

18. The device of claim 5 wherein said body is configured to approximate a size and shape of a nucleus pulposus of a natural intervertebral disc.

19. The implant of claim 5 wherein said biocompatible material is a ceramic material.

20. The implant of claim 19 wherein said biocompatible material is a biphasic calcium phosphate ceramic.

21. The implant of claim 20 wherein said biocompatible material is a hydroxyapatite/tricalcium phosphate ceramic.

22. The implant of claim 19 wherein said ceramic has a porosity of at least about 50%.

23. The implant of claim 22 wherein said ceramic has a porosity of at least about 70%.

24. The implant of claim 19 wherein said ceramic has a mean pore size of about 200 to about 700 microns.

25. The implant of claim 24 wherein said ceramic has a mean pore size of about 300 to about 600 microns.

26. The implant of claim 25 wherein said ceramic has a mean pore size of about 400 microns.

* * * * *